United States Patent [19]
Goodman et al.

[11] Patent Number: 4,837,305
[45] Date of Patent: Jun. 6, 1989

[54] DERIVATIVES OF β-ADRENERGIC ANTAGONISTS

[75] Inventors: Murray Goodman; Debra Marr-Leisy, both of La Jolla; Roberto P. Rosenkranz, Menlo Park; Kenneth L. Melmon, Woodside; Michael S. Verlander, Del Mar, all of Calif.

[73] Assignee: The Regents of the University of California, Berkeley, Calif.

[21] Appl. No.: 85,517

[22] Filed: Aug. 13, 1987

Related U.S. Application Data

[63] Continuation of Ser. No. 733,391, May 10, 1985, which is a continuation of Ser. No. 463,498, Feb. 3, 1983.

[51] Int. Cl.$^4$ .................... C07K 5/00; C07K 13/00; C07C 125/06
[52] U.S. Cl. .................... 530/345; 530/350; 560/28
[58] Field of Search .................... 560/28, 345, 350

[56] References Cited
U.S. PATENT DOCUMENTS
4,687,873 8/1987 Goodman et al. .................... 560/28

*Primary Examiner*—Delbert R. Phillips
*Attorney, Agent, or Firm*—Phillips, Moore, Lempio & Finley

[57] ABSTRACT

Molecular structures of β-adrenergic antagonists are modified to produce biologically active compounds. The β-antagonists are modified to form molecules of the general structure:

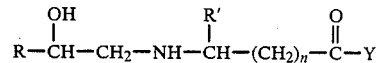

wherein R is most generally R''—OCH$_2$—, and in some instances is R''—, and R''=an aryl or substituted aryl moiety; R'=—H, —CH$_3$, or a short chain alkyl moiety; and Y=—OH, or more usually, —OAX or —NHAX, where A=an alkyl, aryl, or aralkyl moiety, and X=a terminal grouping, such as —CH$_3$, —CF$_3$ or —(CH$_2$)$_n$COOH; or AX may be a carrier moiety consisting of a defined peptide or protein.

12 Claims, No Drawings

DERIVATIVES OF β-ADRENERGIC ANTAGONISTS

This is a continuation of Ser. No. 733,391, filed May 10, 1985, which is a continuation of Ser. No. 463,498, filed Feb. 3, 1983.

BACKGROUND OF THE INVENTION

The β-adrenergic agonist hormones when bound to plasma membrane adrenergic receptor sites (β-sites) produce a broad range of physiological effects such as vasodilation, changes in blood pressure, cardiac stimulation resulting in enhanced cardiac output and rate, increased production of glucose, and initiation of glycogenolysis, etc. These hormones, from a chemical standpoint, are generally classified as catecholamines. That is, they usually possess the characteristic hydroxyl groups substituted at the 3- and 4-positions on a benzene ring and an hydroxyethylamine side chain attached to the number 1 position of the benzene ring.

This invention was made with Government support under Grant No. HL 26340 awarded by the Department of Health and Human Services. The Government has certain rights in this invention.

As noted in U.S. Pat. No. 4,337,207 a number of recently developed derivatives of the naturally occurring catecholamine β-agonist hormones are also capable of producing significant biological and pharmacological effects. Such derivatives include chemically modified and extended hydroxyethylamine side chains wherein an alkyl or alkylaryl chain of variable length is added to the amine and terminates in a carboxylic acid or carboxylic acid derivative functional grouping.

In the past several decades, a group of hormone-like molecules has been synthesized that may also bind at the same β-sites and thereby interfere with, or eliminate, the effects of the β-agonist hormones. These "β-adrenergic antagonist" molecules also play a useful role in the control of the physiological and pathological processes related to this complex hormonal system. For instance, these β-antagonists, when administered to a patient can reduce high blood pressure (hypotensive), restore regular heart rhythm, reduce myocardial work and therefore myocardial oxygenation i.e., they are antianginal.

Like the β-adrenergic agonist hormones, the "β-adrenergic antagonists" may act at both so-called $\beta_1$-receptor sites and $\beta_2$-receptor sites. The $\beta_1$-receptors are generally associated with heart function (e.g. force of contraction); while the $\beta_2$-receptors are usually associated with bronchial smooth muscle and skeletal muscle. The β-adrenergic antagonists therefore may be classified as "nonselective" when they act at both $\beta_1$- and $\beta_2$-receptors; or "cardioselective" (or $\beta_1$-selective) when they act predominantly at $\beta_1$-receptors. In many instances it is desirable to have cardioselective β-adrenergic antagonists available for therapy.

The most common β-adrenergic antagonists have quite closely-related structures that can most often be represented by the general formula:

$$R_1-O-CH_2-\overset{OH}{\underset{|}{CH}}-CH_2-NH-R_2, \quad (I)$$

where $R_1$ is an aryl, or substituted aryl group and $R_2$ is most commonly an isopropyl group; and in a limited number of cases, t-butyl. (In a more limited number of cases β-adrenergic antagonists may be represented by the general formula:

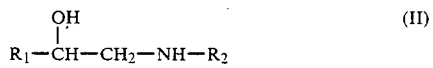

where $R_1$ is a substituted aryl group and $R_2$ is generally isopropyl).

The most common non-selective β-adrenergic antagonists include:

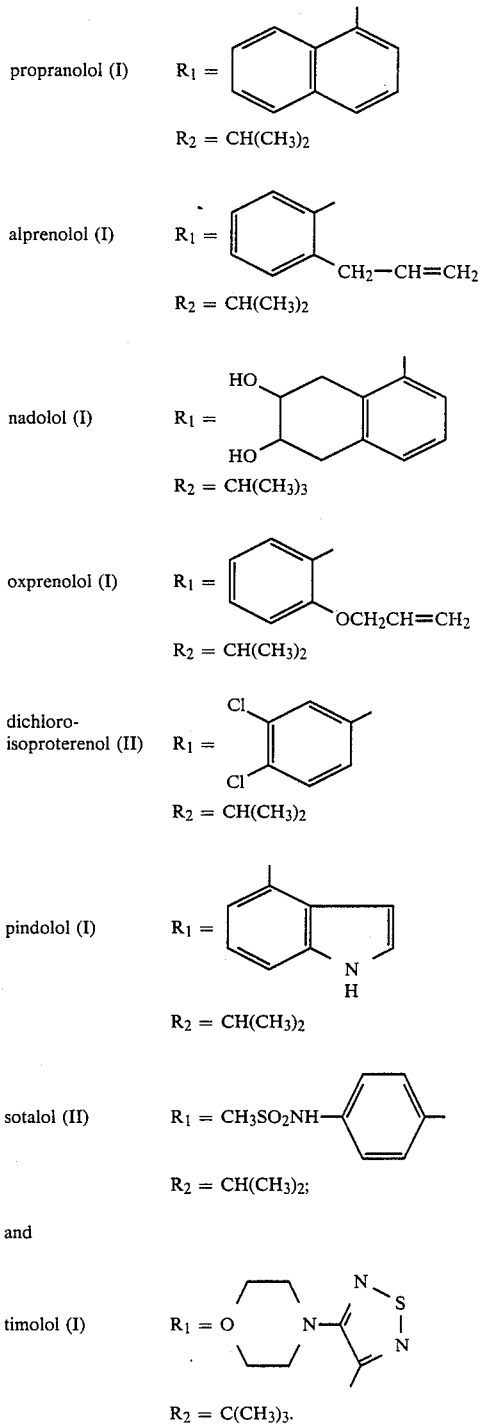

and

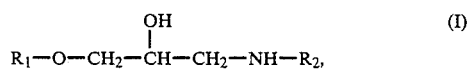

The most common cardioselective β-adrenergic antagonists include:

practolol (I)    $R_1$ = CH₃CONH— 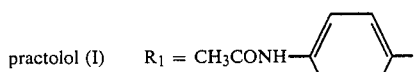

$R_2$ = CH(CH₃)₂ 

atenolol (I)    $R_1$ = H₂NCOCH₂— 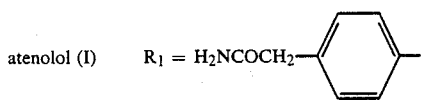

$R_2$ = CH(CH₂)₂ 

metoprolol (I)    $R_1$ = CH₃O(CH₂)₂— 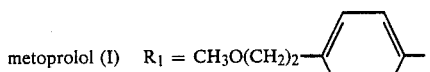

$R_2$ = CH(CH₃)₂ 

celiprolol (I)    $R_1$ = 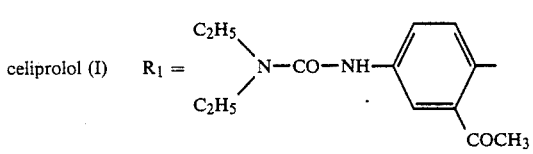

$R_2$ = C(CH₃)₃;

and acebutolol (I)    $R_1$ = CH₃(CH₂)₂—CO—NH— 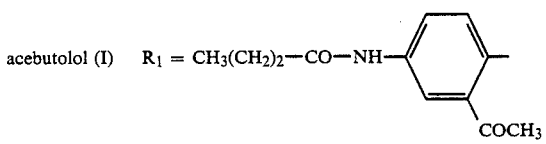

$R_2$ = CH(CH₃)₂. 

In any event all β-adrenergic antagonists exhibit related β-adrenergic properties when introduced into the vascular system. While the structures produce qualitatively similar, but quantitatively different pharmacological effects, in some instances, these effects are diverse and general, but, in others, the effects are very specific. These differences often relate to the different selectivities discussed above.

It is therefore of interest to explore the possibility of devising modified β-adrenergic antagonist molecules which will exhibit biological activities similar to those of the parent compounds; but which might also exhibit enhanced (increased potency), or prolonged (in vivo) activity; or perhaps selective effects which would permit the "targeting" of the drugs or drug effects to selected receptors, tissues, or cells within tissues or a more selective basis than is possible with the parent molecules; or to selected clinical uses wherein the drug effects are narrowed by means of pharmacodynamic or pharmacokinetic differences from the native drug.

It would also be of great interest if structurally modified β-antagonists could be further conjugated with other carrier molecules, e.g., defined peptides or proteins, whereby the conjugate molecules might be degraded less readily by enzymes; or greater tissue or receptor specificity might be imparted because of the drug-carrier properties. The receptors for the β-antagonists are located on the outer surface of cell membranes, and the observed biological effect of the attachment of the antagonists to carrier molecules need not be predominantly dependent upon, nor necessarily be complicated by, complex membrane transport phenomena or phagocytosis of a conjugate molecule. It is therefore possible for covalent conjugates of the β-antagonists to reach the β-receptor sites intact as have their agonist counterparts.

BRIEF DESCRIPTION OF THE INVENTION

The present invention is directed to chemically modified β-adrenergic antagonist structures wherein the side chain N-substituent group is extended by the addition of alkyl or alkylaryl chains of variable length that terminate in a carboxyl group, or more especially, in a substituted amide. These modified, carboxyl-containing β-antagonists may be further modified by covalent binding to carrier molecules, e.g., peptides, to form active conjugate molecules.

As defined herein, a β-antagonist that is chemically modified by extension of the side chain is called a "modified β-antagonist." Where the modification, i.e., extended side chain, terminates in a functional grouping, e.g., a carboxylic acid, the molecule is called a "β-antagonist congener." Where the drug cogener is covalently bound to a carrier molecule, e.g., a peptide or protein, the resultant drug-carrier molecule is called a "drug-conjugate" or "conjugate".

The modified β-antagonists or congeners of the invention have the general structure:

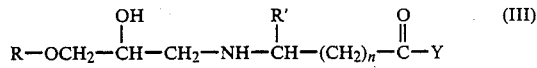  (III)

where
R = an aryl or substituted aryl moiety, e.g.,

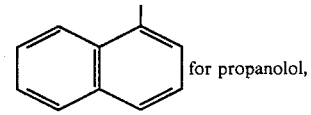 for propanolol,

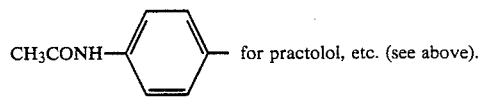 for practolol, etc. (see above).

R' = —H, —CH₃, or lower alkyl moiety; and
Y = —OH, or more especially, O—A—X or —N-H—A—X, where
A = alkyl, aryl, or aralkyl moiety; and
X = a terminal grouping such as —CH₃ or —CF₃; or —(CH₂)ₙCOOH, etc.;
A-X may also be a carrier moiety such as an amino acid or a peptide, e.g., N-acetyl-phenylalanylhydroxypropylamide, t-butyloxycarbonyl-phenylalanylglycylmethylamide, etc.

It is therefore an object of the invention to provide biologically active modifications and congeners, and congener derivatives, such as amides, esters, etc., of β-antagonists.

It is another object of the invention to provide conjugates of β-adrenergic antagonists.

It is another object of the invention to provide β-adrenergic antagonist modifications and cogeners that exhibit β-adrenergic antagonist activity.

It is still another object of the invention to provide conjugates of β-adrenergic antagonists that exhibit β-adrenergic antagonist activity.

It is still another object of the invention to provide β-adrenergic derivatives wherein the molecules are chemically modified by extending the N-substituent group to an alkyl, or alkylaryl chain of variable length and terminating in a carboxyl group or derivative such as a substituted ester or amide group.

It is yet another object of the invention to conjugate β-adrenergic derivatives with peptide carriers.

Others objects and advantages of the invention will be apparent from a review of the following description and the claims appended hereto.

DETAILED DESCRIPTION OF THE INVENTION

The present invention relates to derivatives of β-adrenergic antagonist drugs that exhibit biological activity, or modification of the β-antagonistic activity of the parent compounds. More specifically the invention relates to β-adrenergic antagonist derivatives wherein the terminal N-substituent grouping is modified and extended by the addition of alkyl, or alkylaryl chains of variable length. Such added chains may terminate in a functional group, such as OH, or $NH_2$; or more frequently, in a functional group, such as —COOH, or —$SO_3H$ (congener). In certain instances, the β-adrenergic congener may, in turn, be covalently bound via the terminal functional group to a carrier molecule, e.g., a peptide or protein, to yield a bioactive conjugate.

Generically, the derivatives have the structure:

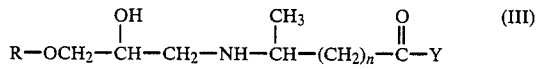

where R = 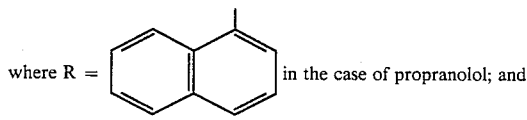 in the case of propranolol; and

R = 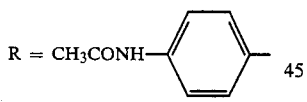

in the case of practolol, etc.; and wherein n indicates the number of methylene groups in the chain, but which is most usually from 1 to perhaps 15; and Y may be either —OH, i.e., a carboxylic acid terminal group; —OAX, i.e., an ester wherein A is an alkyl, aryl, or aralkyl moiety, and X is a terminal grouping such as —$CH_3$, —$CF_3$, $(CH_2)_xCOOH$, etc.; or NH—A—X, i.e., an amide terminal group, wherein A is an alkyl, aryl or aralkyl moiety and X is a terminal grouping, such as $CH_3$, $CF_3$, $(CH_2)_x$—COOH, etc. An aryl amide, i.e.,

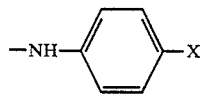

terminal group is especially useful in yielding biologically interesting derivatives.

In some instances, the derivative may be covalently coupled to a carrier moiety through the functional terminal group to form a drug conjugate. If properly selected, the terminal functional group is utilized to connect to the carrier moiety. Completely defined peptides or proteins are especially useful in forming conjugate derivatives, since the biological effect of each amino acid component on the drug-conjugate potency and resistance to catabolic breakdown will be more easily ascertained. The preparation of drug-conjugates will be more fully explained hereinafter.

While it is indicated that the added constituents consist of a spacer moiety and a terminal grouping, it should be noted that the spacer moiety may be a carbon chain that may be straight or branched; and may include aryl groupings, or mixed alkylaryl groupings. The important criterion is the retention or enhancement of β-antagonist activity. In any event, however, the inclusion of a series of methylene groups, i.e., —$(CH_2)_n$— appears to favor the retention of β-antagonist activity.

In the case of the congeners or modified β-antagonists, it is of equal importance that the added N-substituent grouping be terminated in a carboxyl functional grouping, i.e., —COOH; or in a derivative such as an amide, i.e., —CO—NH—R generally; where R can be —H (a primary amide) or a variety or alkyl or aryl groups as outlined below. Such terminal amides may be derived from aromatic amines such as aniline and aniline derivatives, e.g., p-toluidine,

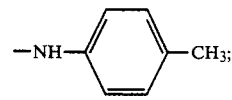

p-trifluoromethyl aniline,

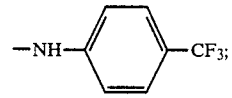

and the amino hydrocinnamic acid derivative,

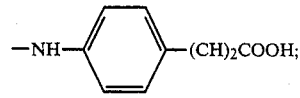

or from aliphatic amines which may be straight chain or branched, e.g. n-butylamine, t-butylamine, etc.

METHODS FOR SYNTHESIZING THE DERIVATIVES

The β-antagonists derivatives having the structure (III)

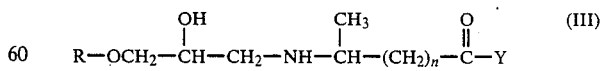

can be synthesized by alkylation reactions, such as reductive amination of an appropriate methyl ketone derivative (II), i.e.,

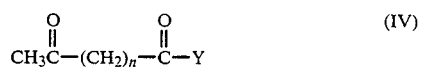

-continued by the compound:

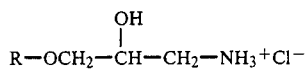
(V)

The reductive amination is effected by the use of NaBH$_3$CN as the reducing agent with methanol as solvent for the reaction compounds; or by catalytic hydrogenation utilizing PtO$_2$/H$_2$ in acetic acid.

Schematically this synthesis may be depicted as:

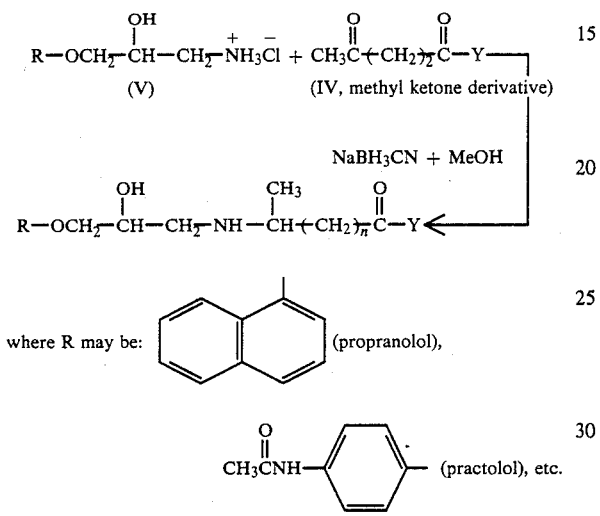

The methyl ketone derivatives (IV) can be synthesized for use in the reductive amination step above by a condensation of the appropriate ketoacid with a suitable amine derivative using the mixed anhydride method. This synthesis may be depicted as:

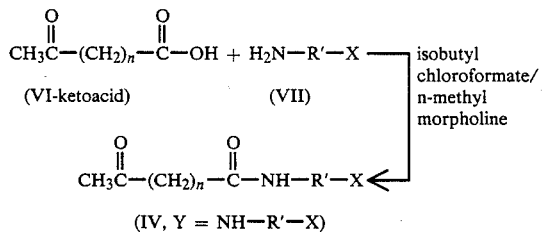

It should be noted that while aromatic amides are preferred aliphatic amides are also useful for this synthesis.

Compounds of the general formula (V) above may be prepared by the following reactions:

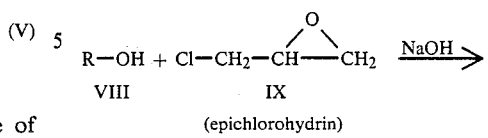

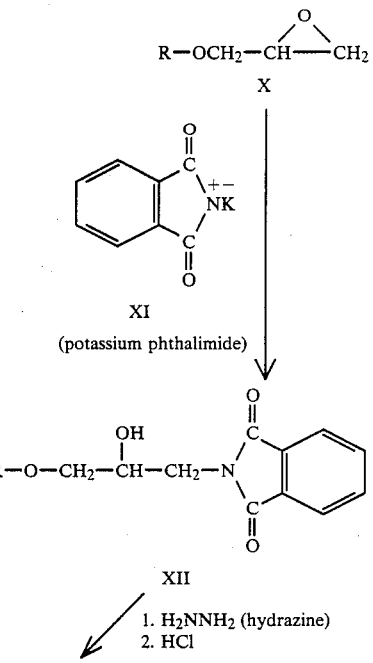

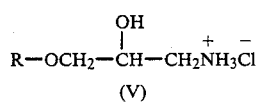
(V)

The group R, which is generally an aryl or substituted aryl moiety, may be derived from a commercially available material or may be synthesized from commercially available starting materials.

Thus, the propranolol precursor (V, R=1-naphthyl) may be synthesized from 1-naphthol as starting material; the synthesis of the precursor for alprenolol congeners utilizes 2-allylphenol; the pindolol precursor utilizes 4-hydroxyindole, etc. Other β-antagonist congener precursors may require more complex syntheses.

For example, the derivative (V), corresponding to the practolol precursor, may be prepared by the following reactions:

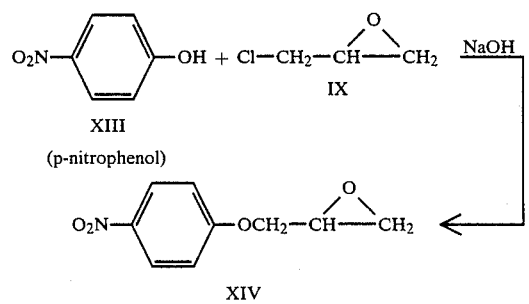

-continued

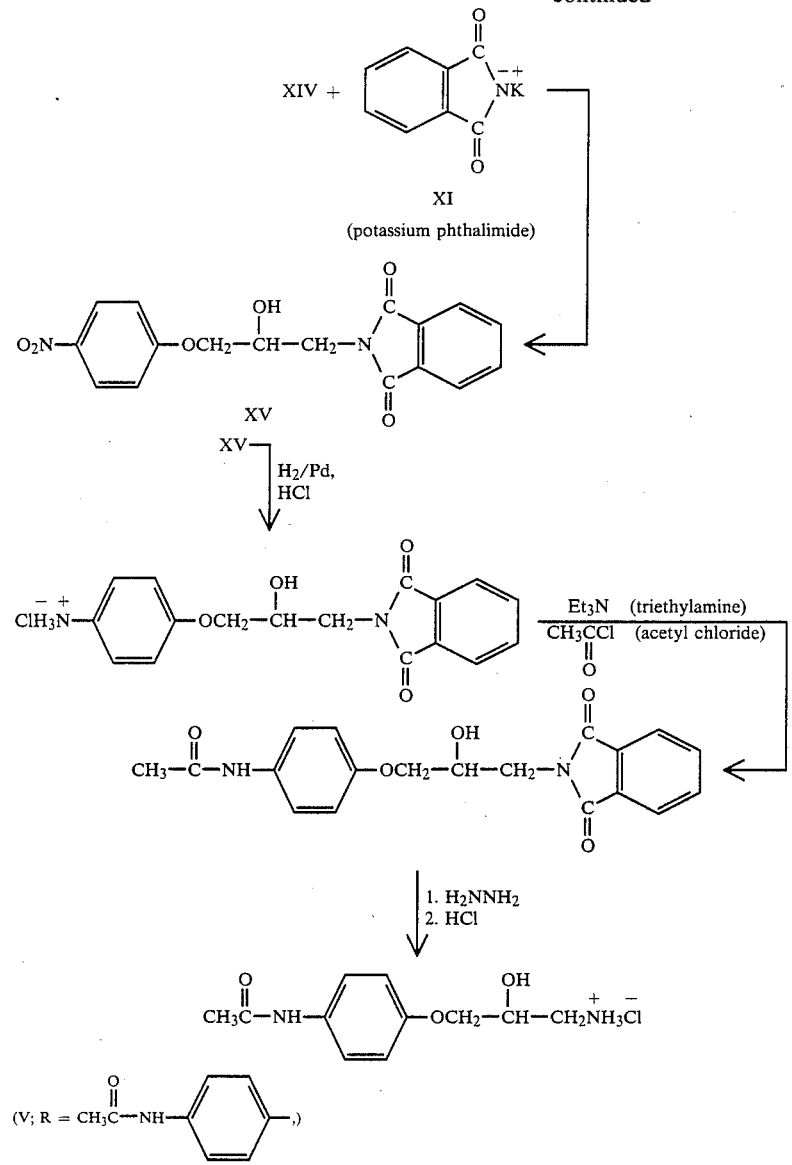

The antagonist derivatives may be purified by conventional purification techniques, such as crystallization, or by chromatographic techniques, such as column chromatography, high pressure liquid chromatography; or flash chromatography may also be used. Such techniques will yield contaminant-free antagonist derivatives.

EXAMPLES

The following examples set forth specific procedures for the preparation of a number of modified β-antagonists, β-antagonist congeners, and congener derivatives in accordance with the invention.

1,2-Epoxy-3-(1-Naphthyloxy)-Propane (Compound X, R=1-naphthyl)

To a solution of β-naphthol (86.09 g. 0.5 mol) and epichlorohydrin (54.6 ml, 0.7 mol) in 200 ml dioxane was added a solution of sodium hydroxide (24.0 g, 0.6 mol) in 50 ml water. The mixture was refluxed for 3 hr during which time sodium chloride precipitated out. The dioxane was evaporated in vacuo and the remaining aqueous solution extracted twice with chloroform. The combined organic fractions were then washed twice with brine and dried over sodium sulfate. After removing the drying agent by filtration, the chloroform was evaporated under reduced pressure. The residual oil showed a major product with only two very minor impurities by thin layer chromatography (95:5:3 chloroform/methanol/acetic acid, $R_f=0.78$) and so was not purified further. Yield: 108 g.

3-(1-Naphthyloxy)-1-Phthalimidopropan-2-ol (Compound XII, R=1-naphthyl)

Compound X (R=1-naphthyl; 45.6 g, 0.20 mol) and phthalimide (29.4 g. 0.20 mol) were mixed in 80 ml n-butanol. To this was added a catalytic amount of potassium phthalimide (0.10 g) and pyridine (1 ml) and the mixture refluxed for 16 hr. Upon cooling, the mixture crystallized to a solid mass which was filtered and washed with chloroform and ether. The light brown solid was boiled in 400 ml ethanol and filtered hot. The insoluble tan material was identified by thin layer chromatography to be almost pure product. Upon cooling more product crystallized from the filtrate. These crops were combined and recrystallized from ethanol to give 21 g of light tan crystals that were homogenous by thin layer chromatography (95:5:3 chloroform/methanol/acetic acid, $R_f=0.65$) m.p. 152°–154° C.

1-Amino-3-(1-Naphthyloxy)-Propan-2-ol Hydrochloride (Compound V, R=1-naphthyl)

Hydrazine hydrate (2.8 g 56 mmol) was dissolved in 100 ml ethanol in a flask which had been flushed with nitrogen. Compound XII (R=1-naphthyl; 21.0 g, 55 mmol) was partially dissolved in 400 ml warm ethanol and the resulting suspension added slowly to the hydrazide solution. After completing the addition, the mixture was warmed gently on a hot plate and within a few minutes the solution became very thick. Ethanol (800 ml) was added and heating was continued for 3 hr. The hydrazine intermediate was destroyed by the dropwise addition of concentrated hydrochloric acid until all the precipitated material dissolved. Upon cooling of the mixture in an ice bath, the phthalylhydrazide precipitated and was separated from the product by filtration. The filtrate was evaporated in vacuo to a white mass which was partially dissolved in water and extracted three times with chloroform. The aqueous phase was then lyophilized and the residue crystallized from ethanol/ether to yield 9 g of white crystals which were shown to be homogenous by thin layer chromatography (50:10:5 chloroform/methanol/acetic acid, $R_f=0.39$) m.p. 201° C. decomp.

1,2-Epoxy-3-(p-Nitrophenoxy)-Propane (Compound XIV)

p-Nitrophenol (139 g, 1.0 mol) was dissolved in 1.5 l 0.8M sodium hydroxide. Epichlorohydrin, IX, (117 ml, 1.5 mol) was added and the mixture stirred vigorously overnight. The homogenous solution was then extracted three times with 300 ml chloroform and the organic fractions combined and dried over magnesium sulfate. After removal of the drying agent by filtration, evaporation of the filtrate gave a yellow oil which crystallized on standing. The oily crystals were triturated with methanol and filtered to yield 55.6 g of the desired compound as white crystals shown to be homogenous by thin layer chromatography (60:40 ethyl acetate/hexanes, $R_f=0.77$) m.p. 62°–65° C.

3-(p-Nitrophenoxy)-1-Phthalimidopropan-2-ol (Compound XV)

Compound XIV (50.0 g, 0.26 mol), phthalimide (37.7 g, 0.26 mol), a catalytic amount of potassium phthalimide (0.1 g) and five drops of pyridine were refluxed in 200 ml absolute ethanol for 1.5 hr. At this time recrystallization of the product commenced and the solution became quite thick. The mixture was filtered hot to remove the crystals and the filtrate heated again to reflux for 8 additional hours. After cooling to room temperature, this solution was filtered to yield 9.6 g additional product giving an overall yield of 79.5 g. The two batches of crystals were combined and triturated with 300 ml boiling ethanol for 1 hr, then filtered hot to give 65.8 g of the desired material which was homogeneous by TLC (95:5:3 chloroform/methanol/acetic acid, $R_f=0.54$) m.p. 173°–176° C.

3-(p-Acetamidophenoxy)-1-Phthalimidopropan-2-ol (Compound XVII)

Compound XV (5.0 g, 14.6 mmol) was hydrogenated in 200 ml ethanol and 50 ml 1N hydrochloric acid on a Parr hydrogenation apparatus at 50 psi with 50 mg 10% palladium on carbon as catalyst. Although the starting material was fairly insoluble in this system, thin layer chromatography showed the absence of starting material after 8 hr. Since the product was also insoluble in the system, the entire mixture was evaporated to dryness, the residue redissolved in 50:50 methanol/dimethylacetamide, and filtered through a Celite pad. Evaporation of the filtrate gave oily crystals which were triturated with hot ethanol. Filtration and drying gave 3.5 g of compound XVI which was homogenous by thin layer chromatography (50:10:5 chloroform/methanol/acetic acid, $R_f=0.79$).

Compound XVI (0.5 g, 1.43 mmol) was suspended in 50 ml anhydrous tetrahydrofuran and the flask flushed with nitrogen. Triethylamine (0.6 ml, 4.29 mmol) was added and the mixture cooled to 0° C. in an ice bath. Acetyl chloride (0.25 ml, 3.58 mmol) was dissolved in 25 ml anhydrous tetrahydrofuran and added dropwise to the above solution via addition funnel. After 1 hr. the mixture was evaporated to dryness, the residue dissolved in 50 ml water plus enough tetrahydrofuran to achieve the dissolution and ethyl acetate added until phase separation occurred. The layers were separated and the organic phase washed twice with 25 ml 1N hydrochloric acid and twice with 25 ml brine. After drying the organic phase over magnesium sulfate for 15 min., filtration and evaporation of the filtrate left a light yellow residue which was crystallized from ethanol/water to give 0.28 g of the title compound as tan, fluffy crystals which were homogeneous by TLC (95:5:3 chloroform/methanol/acetic acid, $R_f=0.32$) m.p. 200°–202° C. decomp.

1-Amino-3-(p-Acetamidophenoxy)-Propan-2-ol Hydrochloride (Compound V, R=p-acetamidophenyl)

Hydrazine hydrate (3.6 g, 0.071 mol) was dissolved in 50 ml ethanol and added slowly to a suspension of Compound XVII (25 g, 0.071 mol) in 300 ml boiling ethanol. After 30 min., all the material dissolved. The temperature of the reaction mixture was reduced to 75° C. and maintained for an additional 1.5 hr. At the end of this time, the mixture was cooled to room temperature and concentrated hydrochloric acid added dropwise to pH 1 (pH paper) to destroy the hydrazide intermediate. Since not all of the material dissolved, the mixture was filtered to remove undissolved phthalhydrazide and the filtrate stored at 4° C. overnight. Filtration of the newly precipitated material gave 10.6 g of the title compound m.p. 192°–197° C. Recrystallization from ethanol/ether yielded 9.0 g of small white cluster crystals which were homogenous by thin layer chromatography (30:10:3:12 butanol/pyridine/acetic acid/water, $R_f=0.46$) m.p. 198.5°–200° C.

1,2-Epoxy-3-(2-Allylphenoxy)-Propane (Compound X, R=2-allylphenyl)

The title compound was synthesized from 2-allylphenol and epichlorohydrin by the method of Brandstrom et al. (Chem. Abs. 72, 12342n).

3-(2-Allylphenoxy)-1-Phthalimidopropan-2-ol (Compound XII, R=2-allylphenyl)

The title compound was prepared from compound X (R=2-allylphenyl) and phthalimide by the general procedure described above for the 1-naphthyl derivative (Compound XII).

1-Amino-3-(2-Allylphenoxy)-Propan-2-ol Hydrochloride (Compound V, R=2-allylphenyl)

Treatment of Compound XII (R=2-allylphenyl) with hydrazine by the method described above for the 1-naphthyl analog (Compound XII) resulted in the title compound.

1,2-Epoxy-3-(4-Indolyloxy)-Propane (Compound X, R=4-indolyl)

The title compound was synthesized from 4-hydroxyindole and epichlorohydrin by the method of Troxler et al. (Chem. Abs. 71, 70493c).

3-(4-Indolyloxy)-1-Phthalimidopropan-2-ol (Compound XII, R=4-indolyl)

Treatment of Compound X (R=4-indolyl) with phthalimide by the general procedure described above for the 1-naphthyl derivative (Compound XII) resulted in the title compound.

1-Amino-3-(4-Indolyloxy)-Propan-2-ol Hydrochloride (Compound V, R=4-indolyl)

The title compound was synthesized from Compound XII (R=4-indolyl) and hydrazine using the general method described above for the 1-naphthyl analog (Compound XII).

1,2-Epoxy-3-[4-($\beta$-Methoxyethyl)-Phenoxy]-Propane [Compound X, R=4-($\beta$-methoxyethyl)-phenyl]

The title compound was synthesized by the method of Brandstrom et al. (Chem. Abs. 76, 10427c)

3-[4-($\beta$-Methoxyethyl)-Phenoxy]-1-Phthalimidopropan-2-ol [Compound XII, R=4-($\beta$-methoxyethyl)-phenyl]

Treatment of Compound X [R=4-($\beta$-methoxyethyl)-phenyl] with phthalimide by the general procedure described above for the 1-naphthyl analog resulted in the title compound.

1-Amino-3-[4-($\beta$-Methoxyethyl)-Phenoxy]-Propan-2-ol Hydrochloride [Compound V, R=4-($\beta$-methoxyethyl)-phenyl]

The title compound was synthesized from Compound XII [R=4-($\beta$-methoxyethyl)-phenyl] and hydrazine using the method described above for the 1-naphthyl analog (Compound XII).

1,2-Epoxy-3-(4-Carboxamidomethylphenoxy)-Propane (Compound X, R=4-carboxamidomethylphenyl)

The title compound was synthesized from 4-hydroxyphenylacetic acid using the method of Barrett et al. (Chem. Abs. 73, 120318p).

3-(4-Carboxamidomethylphenoxy)-1-Phthalimidopropan-2-ol (Compound XII, R=4-carboxamidomethylphenyl)

Treatment of Compound X (R=4-carboxamidomethyl) with phthalimide by the general procedure described above for the 1-naphthyl analog (Compound XII) resulted in the title compound.

1-Amino-3-(4-Carboxamidomethylphenoxy)-Propan-2-ol Hydrochloride (Compound V, R=4-carboxamidomethylphenyl)

The title compound was synthesized from Compound XII (R=4-carboxamidomethylphenyl) and hydrazine using the procedure described above for the 1-naphthyl derivative (Compound XII).

4-Oxopentanoic Acid p-Toluide (Compound IV, n=2, Y=p-methylanilino)

The title compound was prepared by the method described below for 6-oxoheptanoic acid p-toluide (IV, n=4; Y=p-methylanilino) using the following quantities: levulinic acid (5.8 g, 0.05 mmol), N-methylmorpholine (5.5 ml, 0.05 mol), isobutyl chloroformate (6.5 ml, 0.05 mol), p-toluidine (5.4 g, 0.05 mol), tetrahydrofuran (300 ml). Recrystallization from ethyl acetate/hexanes gave 5.7 g of the desired compound as white platelets, which were pure by thin layer chromatography (6:40 ethyl acetate/hexanes, $R_f$=0.48) m.p. 105°–107° C.

5-Oxohexanoic Acid p-Toluide (Compound IV, n=3, Y=p-methylanilino)

The title compound was prepared by the method described below for 6-oxoheptanoic acid p-toluide (IV, n=4, Y=p-methylanilino) using the following quantities: $\gamma$-acetylbutyric acid (0.60 ml, 5.0 mmol), N-methylmorpholine (0.55 ml, 5.0 mmol), isobutyl chloroformate (0.65 ml, 5.0 mmol), p-toluidine (0.54 g. 5.0 mmol), tetrahydrofuran (50 ml). Recrystallization from ethyl acetate/hexanes gave 0.8 g of the desired compound as pale yellow needles, which were pure by thin layer chromatography (95:5:3 chloroform/methanol/acetic acid, $R_f$=0.43) m.p. 120.5°–122.5° C.

6-Oxoheptanoic Acid p-Toluide (Compound IV, n=4, Y=p-methylanilino)

$\delta$-Acetyl-n-valeric acid (1.0 g, 6.9 mmol) was dissolved in 50 ml anhydrous tetrahydrofuran and the solution cooled to 0° C. in an ice bath. N-methyl morpholine (0.76 ml, 6.9 mmol) was added followed by isobutyl chloroformate (0.90 ml, 6.9 mmol). After allowing the reaction to stir for 10 min, p-toluidine (0.74 g, 6.9 mmol) was added and the mixture stirred overnight at room temperature. The solvent was evaporated under reduced pressure and the residue redissolved in 150 ml ethyl acetate and 50 ml water. The organic phase was separated and extracted three times with 50 ml 0.1N hydrochloric acid, three times with 0.1N sodium hydroxide, twice with 50 ml brine and dried over sodium sulfate. After filtration from the drying agent and evaporation of the filtrate, the pale yellow solid was crystallized from ethyl acetate/hexanes yielding 1.2 g of needles that were homogeneous by thin layer chromatography (60:40 ethyl acetate/hexanes, $R_f$=0.31) m.p. 108.5°–110° C.

7-Oxooctanoic Acid p-Toluide (Compound IV, n=5, Y=p-methylanilino)

The title compound was prepared by the method given for 6-oxoheptanoic acid p-toluide (IV, n=4, Y=p-methylanilino) using the following quantities: $\epsilon$-acetylcaproic acid (3.0 g, 19 mmol), N-methylmorpholine (2.1 g. 19 mmol), isobutyl chloroformate (2.5 ml, 19 mmol), p-toluidine (2.0 g. 19 mmol), tetrahydrofuran (50 ml). Recrystallization from ethyl acetate/hexanes gave 4.0 g of the desired compound as off-white platelets, which were pure by thin layer chromatography (95:5:3 chloroform/methanol/acetic acid, $R_f=0.44$) m.p. 108°–109° C.

6-Oxoheptanoic Acid p-Trifluoromethylanilide (Compound IV, n=4, Y=p-trifluoromethylanilino)

The title compound was prepared by the method described for 6-oxoheptanoic acid p-toluide (IV, n=4, Y=p-methylanilino) except that the reaction was refluxed overnight. The following quantities were used: δ-acetyl-n-valeric acid (1.0 g, 6.9 mmol), N-methylmorpholine (1.52, 13.8 mmol), isobutyl chloroformate (0.90 ml, 6.9 mmol), p-trifluoromethylaniline hydrochloride (1.37 g, 6.9 mmol), tetrahydrofuran (50 ml). Recrystallization from ethyl acetate/hexanes gave 1.6 g of the desired compound as pale yellow platelets, which were pure by thin layer chromatography (60:40 ethyl acetate/hexanes $R_f=0.40$) m.p. 138°–140° C.

6-Oxoheptanoic Acid n-Butylamide (Compound IV, n=4, Y=n-butylamino)

The title compound was prepared by the method described for 6-oxoheptanoic acid p-toluide (IV, n=4, Y=p-methylanilino) using the following quantities: δ-acetyl-n-valeric acid (2.5 g, 1.75 mmol), N-methylmorpholine (1.9 ml, 17.5 mmol), isobutyl chloroformate (2.25 ml, 17.5 mmol), n-butylamine (1.7 ml, 17.5 mmol), tetrahydrofuran (15 ml). Recrystallization from ethyl acetate/hexanes gave 1.3 g of the desired compound as white needles, which were pure by thin layer chromatography (95:5:3 chloroform/methanol/acetic acid, $R_f=0.52$) m.p. 53°–54° C.

3-[4-(6-Oxoheptanoylamino)-Phenyl]-Propionic Acid (Compound IV, n=4, Y=3-p-aminophenylpropionic acid)

The pentachlorophenyl ester of δ-acetyl-n-valeric acid (29 g, 0.074 mol) and 1-hydroxy-benzotriazole (10 g, 0.074 mol) were dissolved in 100 ml anhydrous tetrahydrofuran and the solution cooled to 0° C. in an ice bath. The hydrochloride salt of p-aminocinnamic acid (14.8 g, 0.074 mol) was dissolved in 50 ml anhydrous dimethylformamide and triethylamine (20.6 ml, 0.148 mol) was added. This solution was then added to that containing the active ester and the mixture allowed to warm to room temperature. After 24 hr. the mixture was filtered and the filtrate evaporated under reduced pressure to a slurry which was dissolved in 0.2N sodium hydroxide. The basic solution was extracted three times with chloroform and then cooled in an ice bath before acidifying to pH 3 (pH paper) with 1N hydrochloric acid. The precipitate was isolated by filtration and washed with water and then dissolved in hot methanol. The solution was allowed to cool to room temperature, then stored in the freezer overnight. Filtration and drying yielded 10.6 g of 4-(6-oxoheptanoylamino)-cinnamic acid which was homogeneous by thin layer chromatography (95:5:3 chloroform/methanol/acetic acid, $R_f=0.44$) m.p. 222°–225° C.

The above material (10.6 g, 36.6 mmol) was subjected to catalytic hydrogenation at atmospheric pressure in 500 ml methanol using 10% palladium on carbon as catalyst. After 16 hr, the solution was filtered through a Celite pad and the solvent evaporated under reduced pressure. The residue was crystallized from ethyl acetate/hexanes to give 9.9 g of the title compound. Recrystallization from the same solvents gave material homogeneous by thin layer chromatography (95:5:3 chloroform/methanol/acetic acid, $R_f=0.24$) m.p. 148°–159.5° C.

Examples of the preparation of β-antagonist derivatives and congeners:

4-[3-(1-Naphthyloxy)-2-Hydroxypropylamino]-Pentanoic Acid p-Toluide (Compound 7)

Compound V (R=1-naphthyl) (0.38 g, 1.5 mmol) and 4-oxopentanoic acid p-toluide (0.31 g, 1.5 mmol) were suspended in 3 ml anhydrous methanol and the flask flushed with nitrogen. Sodium cyanoborohydride (0.094 g, 1.5 mmol) was dissolved in 2 ml methanol and added to the above mixture. After heating the reaction for 24 hr at 55° C. in an oil bath, 1N hydrochloric acid was added to pH 2 (pH paper) to destroy excess cyanoborohydride. After bubbling subsided the solution was added to 50 ml 0.1N hydrochloric acid (an opaque emulsion resulted) and extracted once with 20 ml ether and once with 20 ml chloroform. The chloroform extract was evaporated leaving a pale yellow oil which was subjected to flash chromatography using a 30 mm×7 inch column of silica gel 60 (230–400 mesh), 70:5:3 chloroform/methanol/acetic acid as eluant, and a solvent head drop rate of 2 in/min. The appropriate fractions were collected and the solvent evaporated under reduced pressure to leave a colourless thick oil which was redissolved in 50 ml chloroform and extracted twice with 10 ml 0.1N hydrochloric acid to remove any silica gel from the solution. Evaporation of the chloroform under reduced pressure and lyophilization of the residue from methanol/water gave 0.91 g of Compound 7 as a white powder which was pure by analytical high pressure liquid chromatography on a $C_{18}$ column with a flow rate of 2.0 ml/min using 65% methanol/0.01N hydrochloric acid as eluant (ret. time=17.5 min) and by thin layer chromatography (80:5:3 chloroform/methanol/acetic acid, $R_f=0.29$).

5-[3-(1-Naphthyloxy)-2-Hydroxypropylamino]-Hexanoic Acid p-Toluide (Compound 8)

The title compound was synthesized and purified by the method described for Compound 7 using the following quantities: Compound V (R=1-naphthyl) (0.38 g, 1.5 mmol), 5-oxohexanoic acid p-toluide (0.33 g, 1.5 mmol), sodium cyanoborohydride (0.094 g, 1.5 mmol), methanol (3 ml). Evaporation of the final chloroform phase under reduced pressure gave 0.27 g of the hydrochloride salt of the desired compound as a white glass/foam which was pure by analytical high pressure liquid chromatography ($C_{18}$ column, 65% methanol/0.01N hydrochloric acid, 3.0 ml/min flow rate, ret. time=13 min) and thin layer chromatography (80:5:3 chloroform/methanol/acetic acid, $R_f=0.29$).

6-[3-(1-Naphthyloxy)-2-Hydroxypropylamino]-Heptanoic Acid p-Toluide (Compound 9)

6-Oxoheptanoic acid p-toluide (0.050 g, 0.21 mmol) and Compound V (R=1-naphthyl) (0.046 g, 0.21 mmol) were dissolved in 1.5 ml glacial acetic acid in a 10 ml round bottom flask which had been flushed with nitrogen. Platinum dioxide (2 mg) was added as catalyst and the mixture hydrogenated at atmospheric pressure for 18 hr. The solution was then filtered to remove platinum and the filtrate made up to 50 ml with 0.1N hydrochloric acid. The aqueous solution was extracted 3 times with 30 ml chloroform and the chloroform fractions combined and evaporated to a glass, a portion of which was subjected to high pressure liquid chromatography for purification (semipreparative $C_{18}$ column, 3.8 ml/min, 60% methanol/0.01N hydrochloric acid). The appropriate fractions were combined, the solvent evaporated under reduced pressure, and the residue lyophilized from methanol/water to give 12.3 mg of the hydrochloride salt of the desired compound.

7-[3-(1-Naphthyloxy)-2-Hydroxypropylamino]-Octanoic Acid-p-Toluide (Compound 10)

The title compound was synthesized by the method described for Compound 7 using the following quantities: Compound V (R=1-naphthyl) (0.254 g, 1.0 mmol), 7-oxooctanoic acid p-toluide (0.247 g, 1.0 mmol), sodium cyanoborohydride (0.063 g, 1.0 mmol), methanol (7.5 ml). After the usual extractions the chloroform fractions were combined and evaporated under reduced pressure to a white foam which was redissolved in a minimal amount of chloroform. After standing at 4° C. overnight, a very fine precipitate separated out which was removed from the solvent by filtration and dried giving 0.116 g of the hydrochloride salt of the desired compound. The purity of the product was verified by thin layer chromatography (95:5:3 chloroform/methanol/acetic acid, $R_f=0.24$) and high pressure liquid chromatography ($C_{18}$ column, 64% methanol/0.01N hydrochloric acid, 2.0 ml/min flow rate, ret. time=25 min).

6-[3-(1-Naphthyloxy)-2-Hydroxypropylamino]-Heptanoic Acid p-Trifluoromethylanilide (Compound 11)

The title compound was synthesized by the method given for Compound 7 using the following quantities: Compound V (R=1-naphthyl) (0.076 g, 0.3 mmol), 6-oxoheptanoic acid p-trifluoromethylanilide (0.086 g, 0.3 mmol) sodium cyanoborohydride (0.019 g, 0.3 mmol), 5% glacial acetic acid in methanol (4 ml). Purification after extraction was achieved by semipreparative high pressure liquid chromatography using a $C_{18}$ column, 3.0 ml/min flow rate, with 64% methanol/0.1N hydrochloric acid as eluant. The appropriate fractions were combined, evaporated under reduced pressure and lyophilized from methanol/water to give 6.6 mg of the hydrochloride salt of the desired compound. The purity of the product was verified by HPLC (3.5 ml/min, 64% methanol/0.1N hydrochloric acid, ret. time=32 min).

3-{p-(6-[3-(1-Naphthyloxy)-2-Hydroxypropylamino]-Heptanoylamino)-Phenyl}-Propionic Acid (Compound 12)

Compounds V (R=1-naphthyl) (0.10 g, 0.39 mmol) and IV (n=4, Y=p-aminophenylpropionic acid) (0.115 g, 0.39 mmol) were dissolved in 4 ml anhydrous methanol and the flask flushed with nitrogen. Sodium cyanoborohydride (0.025 g, 0.39 mmol) was then added and the mixture heated at 55° C. overnight in an oil bath. To destroy any remaining cyanoborohydride, 3N hydrochloric acid was added to pH 2 (pH paper) and the mixture stirred for 10 min. The solution was then dissolved in 50 ml 0.1N hydrochloric acid and extracted three times with 15 ml ether and three times with 15 ml chloroform. Thin layer chromatography showed the majority of the product still remained in the aqueous phase so this was extracted three times with 15 ml n-butanol. The butanol was evaporated under high vaccum and the residue subjected to flash chromatography for purification. The chromatography was performed using a 30 mm×6 in column of silica gel 60 (230-400 mesh) with 95:10:5 chloroform/methanol/acetic acid as eluant and solvent head drop rate of 2 in/min. The appropriate fractions were collected and the solvent removed in vacuo. The residue was lyophilized from methanol/0.1N hydrochloric acid to yield 0.01 g of the title compound as the hydrochloric salt showing greater than 95% purity as analyzed via high pressure liquid chromatography. This analysis was carried out using a semi-preparative $C_{18}$ column at a flow rate of 2.0 ml/min using 65% methanol/0.1N hydrochloric acid as eluant. The product had a retention time of 11.2 min.

3-{p-(6-[3-(1-Naphthyloxy)-2-Hydroxypropylamino]-Heptanoylamino)-Phenyl}-Propionic Acid n-Butylamide (Compound 13)

Compound 12 (38 mg, 0.07 mmol) and N-hydroxysuccinimide (17 mg, 0.14 mmol) were dissolved in 1.0 ml anhydrous dimethylformamide. Dicyclohexylcarbodiimide (30 mg, 0.15 mmol) was dissolved in 1.0 ml dimethylformamide and the solution added dropwise. The flask was then flushed with nitrogen, capped and allowed to stir at room temperature overnight. At this time, thin layer chromatography showed only a trace of the starting acid and a major new spot corresponding to the hydroxy succinimide ester. N-butylamine (7.1 1, 0.07 mmol) was then added to the mixture. After 4 hr the solution was decanted from the precipitated dicyclohexylurea and evaporated to an oil in vacuo. The oil was dissolved in a small amount of chloroform, added to 50 ml 0.1N hydrochloric acid and the mixture extracted twice with 30 ml ether and three times with 25 ml chloroform. The chloroform fractions were combined and evaporated under reduced pressure to yield 59 mg of a glassy material. Purification of a portion of this material was effected by semipreparative high pressure liquid chromatography using a $C_{18}$ column, flow rate of 1.3 ml/min and a solvent gradient of 58-64% methanol/0.01N hydrochloric acid. Removal of the solvent in vacuo and lyophilization from methanol/water gave 5 mg of the title compound as the hydrochloride salt which was pure by analytical high pressure liquid chromatography (using the above column, flow rate of 20 ml/min, isocratic solvent system of 64% methanol/0.01N hydrochloric acid, ret. time=14.6 min.).

6-[3-(1-Naphthyloxy)-2-Hydroxypropylamino]-Heptanoic Acid n-Butylamide (Compound 14)

The title compound was synthesized by the method given for Compound 7 using the following quantities: Compound V (R=1-naphthyl) (0.177 g, 0.5 mmol), 6-oxoheptanoic acid n-butylamide (0.100 g, 0.5 mmol), sodium cyanoborohydride (0.32 g, 0.5 mmol), methanol (2 ml). Purification of a portion of the product after extraction was achieved by semipreparative high pressure liquid chromatography using a $C_{18}$ column, 1.3 ml/min flow rate with 64% methanol/0.01N hydrochloric acid as eluant. The appropriate fractions were combined, the solvent evaporated under reduced pressure and the residue lyophilized from methanol/water to give 13.8 mg of the hydrochloride salt of the desired compound. The purity of the product was verified by HPLC (1.2 ml/min, 64% methanol/0.01N hydrochloric acid, ret. time=20 min).

6-[3-(4-Acetamidophenoxy)-2-Hydroxypropylamino]-Heptanoic Acid p-Toluide (Compound 17)

Compound V (R=p-actamidophenyl) (0.065 g, 0.25 mmol) and 6-oxoheptanoic acid p-toluide (0.058 g, 0.25 mmol) were dissolved in 5 ml anhydrous methanol and the flask flushed with nitrogen. To this solution was added sodium cyanoborohydride (0.016 g, 0.25 mmol). The vessel was capped and the mixture stirred overnight at 45° C. in an oil bath. To destroy excess cyanoborohydride, 3N hydrochloric acid was added to pH 2 (pH paper) and the mixture stirred for 10 min. The solution was then taken up into 40 ml 0.1N hydrochloric acid and extracted once with 25 ml ethyl acetate and twice with 20 ml n-butanol. The butanol fractions were combined and evaporated under reduced pressure to a glass which was re-dissolved in water and lyophilized to give 0.119 g of a white solid. Further purification was achieved by high pressure liquid chromatography using a semi-preparative $C_{18}$ column, flow rate of 1.5 ml/min, and 52% methanol/0.01N hydrochloric acid as eluant. The appropriate fractions were combined and the solvent evaporated under reduced pressure. Lyophilization, of the residue from water gave 20 mg of Compound 17 which was shown to be pure by analytical HPLC with a retention time of 21 min.

6-[3-(4-Acetamidophenoxy)-2-Hydroxypropylamino]-Heptanoic Acid p-Trifluoromethylanilide (Compound 18)

The title compound was synthesized by the method given for Compound 16 noted in the examples for the preparation of conjugates below. The following quantities were used: Compound V (R=p-acetamidophenyl) (0.065 g, 0.25 mmol), 6-oxoheptanoic acid p-trifluoromethylanilide (0.072 g, 0.25 mmol), sodium cyanoborohydride (0.016 g, 0.25 mmol), methanol (5 ml). Purification of a portion of the material was achieved by high pressure liquid chromatography using a semi-preparative $C_{18}$ column, flow rate of 1.5 ml/min, and solvent system of 52% methanol/0.01N hydrochloric acid. The appropriate fractions were combined and the solvent evaporated under reduced pressure. Lyophilization of the residue from water gave 7.9 mg of the hydrochloride salt of the product, which was shown to be pure by analytical HPLC (same conditions, ret. time=38 min) and thin layer chromatography (50:10:5 chloroform/methanol/acetic acid, $R_f=0.27$).

6-[3-(2-Allylphenoxy)-2-Hydroxypropylamino]-Heptanoic Acid p-Toluide

The title compound was synthesized from Compound V (R=2-allylphenyl) and 6-oxoheptanoic acid p-toluide on a 1.5 mmol scale using the general procedure described above for Compound 7.

6-[3-(4-Indolyloxy)-2-Hydroxypropylamino]-Heptanoic Acid p-Toluide

The title compound was synthesized from Compound V (R=4-indolyl) and 6-oxoheptanoic acid p-toluide on a 1 mmol scale by the procedure described for Compound 9, using 10% palladium on carbon in place of platinum dioxide as catalyst.

6-[3-(4-β-Methoxyethylphenoxy)-2-Hydroxypropylamino]-Heptanoic Acid p-Toluide The title compound was synthesized from Compound V [R=4-(β-methoxyethyl)-phenyl] and 6-oxoheptanoic acid p-toluide on a 2 mmol scale using the general procedure described above for Compound 7.

6-[3-(4-Carboxyamidomethylphenoxy)-2-Hydroxypropylamino]-Heptanoic Acid p-Toluide The title compound was synthesized from Compound V (R=4-carboxamidomethylphenyl) and 6-oxoheptanoic p-toluide on a 0.5 mmol scale using the general procedure described above for Compound 7.

The conjugates of β-antagonists

The present invention also contemplates the preparation of conjugates linking the functionalized antagonist drug (congener), e.g., a propranolol or practolol derivative, etc. to a carrier molecule, e.g., a peptide or protein, by covalent bonds. A functional spacer is utilized for covalent linkage to the drug and to the carrier, yet it does not interfere with the pharmacological properties of the drug. It also provides a chemically stable linkage with the carrier; and facilitates good yields of the conjugate.

The conjugates of the invention may be most easily conceptualized from the following:

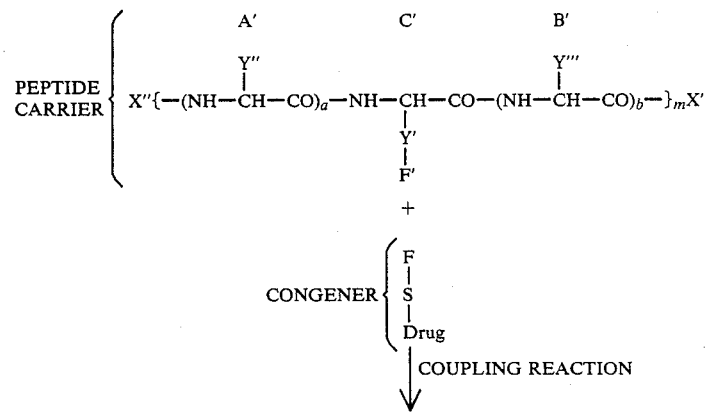

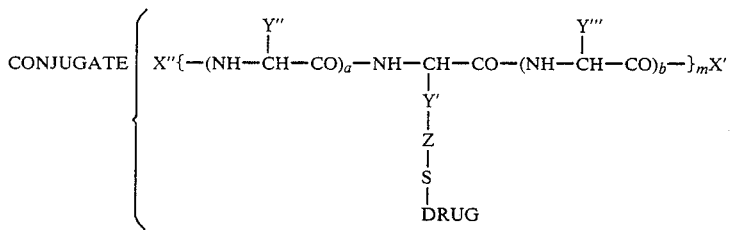

where:
- S is a schematic representation of the spacer group attached to the drug;
- F is a schematic representation of the functional group attached to the spacer, where Drug-S-F comprises the congener;
- F' is a schematic representation of a functional group attached to the carrier side chain, Y', of the amino acid residue to which the congener is bound in the conjugate and wherein the functional group F' is reactive with functional group F;
- Z is a schematic representation of the reacted groups F and F' or chemical bond whereby the congener is bound to the carrier;
- A', B' are oligopeptide blocks wherein the amino acid residues are the same, or different with predesigned sequences;
- C' is an amino acid residue to which the congener is bound;
- X" is an amine blocking group, or -H;
- X' is a carboxyl blocking group, or -H;
- Y" is a general amino acid residue side chain;
- Y''' is a general amino acid residue side chain;
- Y' is a side chain on the amino acid residue to which the congener is bound;
- $a=b$; $a=b$; a or b can be 0, or any small integer; and $m=1, 2, 3$, etc.

As will be apparent from the general structure above, the drug is bound via a spacer S and reacted functional group moiety, Z, to the C' amino acid residue side chain Y' of the carrier peptide A'—C'—B'. The carrier consists of a monodisperse peptide (i.e. one whose sequence and chemical structure are completely defined) wherein blocks A' and B' may be homo-oligopeptide blocks, i.e., wherein the amino acid residues are identical, or alternately, several different amino acid residues in a predetermined sequence. A particular amino acid residue, C', is located at a predetermined position in the peptide chain. Amino acid residue, C', which consists of a single amino acid residue, is selected to be reactive with the particular congener to be attached to the carrier.

It should also be understood that the peptide carrier blocks A", B' and C' may be linked with homologous blocks A', B' and C' to form carrier peptides of increasingly greater molecular weights, e.g., [A'—C'—B']$_m$[A'—C'—B']$_q$, where $m=1, 2, 3$, etc. and $q=0, 1, 2, 3$, etc. and where the sequence of blocks A', B', and C' in the peptide chain may be of any desired order. Furthermore, it should be understood that, when carriers of increasing molecular weight are used, not all of the potential sites of attachment or drug molecules (amino acid residue C'), need be derivatized with drug. It should also be understood that peptide blocks A'—C'—B' may be linked to a defined peptide sequence D, such as a naturally occurring peptide or protein. Thus any desired molecular weight or sequence of monodisperse peptides may be utilized as the carrier moiety of the conjugate.

It should also be understood that the carrier may consist of a single blocked amino acid residue, C', alone. Selection of the number of amino acid residues and their identity will be discussed hereinafter. Generally speaking, however, carrier moieties having molecular weights in the range of $2 \times 10^2$ to $10^4$ daltons seem to be most suited for maintaining the rapid onset of biological activity in vivo. Nonetheless carrier molecular weights of $10^5$ daltons or greater are also contemplated for use in the conjugates of this invention.

Naturally-occurring monodisperse peptides are also contemplated for use as carriers for drugs in the manner already described for synthetic, monodisperse carriers. Thus, peptide hormones and proteins are useful in this context since they naturally contain functional groups (e.g., amine or carboxyl groups) provided by the side chains of their constituent amino acids. Antibodies, especially monoclonal antibodies, are particularly useful as carriers for drugs since, because of their specificity for particular cells, they can be used to target the drugs and thereby optimize the activity of the drug while minimizing or eliminating side effects.

The spacer moiety may include an alkyl, aryl, arylalkyl, alkenyl, polyenyl group, etc. so long as said group does not interfere with the coupling of the congener to the carrier. It is also advantageous that the spacer group incorporate a branched chain immediately adjacent to the amine group of the drug. The spacer moiety must be capable of covalently bonding to the terminal end of the amine side chain of the drug; while also being capable of covalently bonding to the reactive group of the carrier molecule.

The spacer moiety attached to the drug may be any group as noted above. The initial end of the spacer moiety must be capable of covalently bonding to the terminal end of the amine side chain of the drug; while its terminal end must be bonded to a functional group, which group must, in turn, be capable of covalent bonding to side chain Y', of the carrier amino acid residue, C'. The functional group terminal end is chosen to be complementary to the functional group terminating side chain, Y' of the carrier amino acid residue, C'. Thus if residue C' side chain contains an amine functional grouping, e.g., lysine or p-aminophenylalanine, the terminal functional grouping of the attached functional group may be a carboxyl, a sulfonic acid, etc.

The number of drug congeners per conjugate molecule may be one, or any number greater than one. Wherever an amino acid residue, C', is placed within the carrier structure a drug congener may be attached thereto. The greater the number of the C' amino acid residues present in the carrier the greater the number of drug congeners that may be attached. The spacing between the drug congeners on any conjugate molecule may also be controlled by the spacing of the C' amino acid residues on the carrier blocks or, as noted above, by the inclusion of C' amino acid residues which are not derivatized with the drug. Thus the size and sequence of the oligopeptide blocks A' and B' (note the variables a and b in the general structure diagram above) will determine the spacings between the C' peptide residues and thus the spacings between the attached drug congeners. Similarly, the sequence in which the oligopeptide blocks A', B' and C' are present in the carrier molecule will also determine the distances between attached drug congeners.

Similarly, when naturally-occurring, monodisperse peptides are used as carriers, although the sites of attachment may remain constant, because of the defined sequence of the peptide or protein, the number of drug molecules per carrier molecule may be controlled through the stoichiometry used during the coupling reaction.

The amino acid residues in the synthetic peptide carrier molecule may be present either in the L-form or in the D-form, or as a mixture of both forms. Incorporation of D-amino acid residues into the carrier increases proteolytic resistance of the conjugates in vivo. Increased proteolytic resistance should also affect the duration of the effect of the attached drug.

Generally, the conjugates of the invention are synthesized by one of two routes. The first method involves the preparation of appropriate congeners wherein the extended amino side chain of the drug has a suitable spacer moiety terminated in a functional group added to the amino end of the drug. The functionalized drug i.e., the congener, is then, in turn, coupled to the side chain Y' of the C' amino acid residue in the carrier peptide. The second method of synthesis involves the initial modification of the carrier peptide by coupling the spacer-functional group moiety directly to the side chain, Y', of the C' amino acid residue. The resulting peptide-functional group-spacer is then coupled directly to the $\beta$-antagonist, for example, by a reductive animation reaction to produce the peptide-drug conjugate.

The structure and preparation of conjugates of the $\beta$-antagonists may be understood by reference to a specific series of monodisperse conjugates wherein propanolol and practolol congeners or congeners of other $\beta$-blocking molecules (the drugs) are linked to monodisperse peptides (the carrier) to provide $\beta$-antagonist conjugates. The synthesis of the conjugates is accomplished by any of several routes wherein (1) the drug molecule is first modified to produce a congener thereof as noted above. The modification of the drug to form the congener comprises linking the desired spacer grouping to the drug. The spacer grouping is terminated by a functional group which is then linked to a suitable amino acid residue on the carrier molecule; or (2) the carrier molecule has the spacer grouping linked to a predetermined amino acid residue in the carrier peptide chain and the drug molecule is then allowed to react with the functionalized carrier to form the desired conjugate. The second route is generally preferred in the case of small synthetic carriers because of increased yields and a decreased chance of degrading the pharmacophore portion of the drug during conjugate formation.

However, in the case of naturally-occurring peptide carriers, such as peptide hormones and proteins, the first route may be preferred because of the potential sensitivity of the carrier to degradation or decomposition (including denaturation) during the linking reaction of the drug to the prefunctionalized carrier in route (2).

The second method involves first attaching a keto-acid to the carrier peptide. The functionalized peptide carrier is then linked to the drug by reductive amination.

More specifically and for purposes of illustration, a simple conjugate i.e., propranolol linked to a single amino acid e.g. p-aminophenylalanine may be considered. In this illustration the alpha amine and carboxylic acid ends of p-aminophenylalanine are blocked by acetyl and 3-hydroxypropylamide groups respectively. The 3-hydroxypropylamide group enhances water solubility of the resultant conjugate.

In the actual procedure the amino acid, p-nitrophenylalanine is first converted to the N-acetyl methyl ester derivative in two steps. One of two alternate methods may be used. In the first of these, esterification is carried out by the method disclosed by Guttman and Boissonnas in Helv. Chim. Acta. 41, 1852–1867 (1958) followed by pyridine-catalyzed acetylation. In the second method, the amino acid is first acetylated with acetic anhydride in cold, aqueous base without racemization by the procedure as set forth by Yoshida and Ishii in J. Biol. Chem. 71, 185–191 (1972). The N-acetyl-p-nitrophenylalanine is then esterified by diazomethane.

The N-acetyl methyl ester derivative, either in the L- or D-form is then converted to the 3-hydroxypropylamide by aminolysis with excess of 3-amino-1-propanol.

The methyl ketone functional grouping is attached to the acetyl amino acid hydroxypropylamide derivative by catalytic reduction of the nitro group followed by coupling to a keto-acid such as 6-oxo-n-heptanoic acid. The methyl ketone functionalized amino acid carrier molecule is then subjected to catalytic reductive amination with "nor-propranolol" (Compound V, R=1-naphthyl) in the presence of sodium cyanoborohydride to yield the propranolol amino acid conjugate. The resultant conjugate is purified by utilizing high pressure liquid chromatography or other chromatographic methods.

Similar techniques to those outlined above, may be utilized to prepare conjugates of the $\beta$-antagonists with carrier molecules having multiple amino acid residues forming the peptide. Several of such preparations are set forth in the examples hereinbelow.

Preparation of Peptide Carriers

The following examples illustrate the various methods which may be used for producing monodisperse peptide carriers.

p-Nitro-L-Phenylalanine Methyl Ester Hydrochloride (Compound 1)

Thionyl chloride (distilled, 0.69 ml, 9.5 mmol) was added dropwise to methanol (20 ml) at 31 10° C. p-Nitro-L-phenylalanine (1.00 g, 4.76 mmol) was added and the solution stirred 24 hours at room temperature. After evaporating to dryness, the residue was recrystallized from methanol/ether to give 1.00 g of a white solid melting at 218°–219° C. $[\alpha]^{25} = +11.5°$ (c=0.9, H$_2$O).

N$^\alpha$-Acetyl-p-Nitro-L-Phenylalanine Methyl Ester (Compound 2)

Compound 1 (4.10 g, 15.7 mmol) was suspended in a mixture of distilled pyridine (40 ml) and acetic anhydride (5 ml). The solid dissolved after several minutes and stirring was continued overnight. The solvent was evaporated under reduced pressure and the residue dissolved in ethyl acetate. The mixture was then extracted with 0.1N hydrochloric acid, 1M sodium bicarbonate, and water and dried over magnesium sulfate. Removal of the drying agent by filtration and precipitation of the product with hexanes gave 3.57 g of a solid melting at 113°–117° C. Recrystallization from ethyl acetate/hexanes gave 2.75 g of the desired compound. $[\alpha]_D^{25} = +15.1°$ (c=2.1, ethanol); m.p. 118°–120° C.

$N^\alpha$-Acetyl-p-Nitro-L-Phenylalanyl-3-Hydroxypropylamide (Compound 3)

Compound 2 (0.33 g, 1.2 mmol) and 3-amino-1-propanol (1.5 ml, 20 mmol) were dissolved in methanol (12 ml) and stirred for 12 h under nitrogen at room temperature. The solution was loaded onto a column (2×8 cm) of Dowex 50×1-8 in the hydrogen form and eluted with methanol. Evaporation of the solvent under reduced pressure left a light yellow solid which was recrystallized from ethyl acetate/hexanes to give 0.29 g of the desired compound. $[\alpha]^{26} = +14.8°$ (c=1.4, ethanol); m.p. 206.5°–207° C.

$N^\alpha$-Acetyl-p-(6-Oxoheptanoylamino)-L-Phenylalanyl-3-Hydroxypropylamide (Comppound IV, n=4,

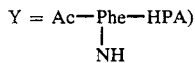
$$Y = \text{Ac}-\underset{\underset{\text{NH}}{|}}{\text{Phe}}-\text{HPA})$$

Compound 3 (0.130 g, 0.42 mmol) was dissolved in methanol and hydrogenated at atmospheric pressure with 10% palladium on carbon as catalyst. After the reduction was complete as shown by thin layer chromatography (65:35:4 chloroform/methanol/water) the solution was filtered through a Celite pad and the filtrate evaporated under reduced pressure to a clear glass. The amine (0.117 g, 0.42 mmol) was dissolved in distilled dimethylformamide (10 ml) and 6-oxoheptanoic acid pentafluorophenyl ester (0.25 g, 0.81 mmol) was added. After a catalytic amount of 1-hydroxybenzotriazole (0.010 g) was added, the solution was stirred at room temperature overnight. The solvent was then evaporated under reduced pressure, the residue dissolved in water, and the solution extracted three times with chloroform and three times with n-butanol. The butanol fractions were combined and evaporated to a white solid which was recrystallized from methanol/ether to give 0.069 g of the desired compound. (85:10:5 chloroform/methanol/acetic acid, $R_f$=0.34), mp. 153°–159° C.

$N^\alpha$-t-Butyloxycarbonyl-p-Nitro-L-Phenylalanine (Compound 4)

p-Nitro-L-phenylalanine (51.3 g, 0.25 mol) was stirred in ice-cold sodium hydroxide (1N, 245 ml). Dioxane (200 ml) and di-t-butyl-dicarbonate (60.0 g, 0.28 mol) were added. After stirring overnight in the cold the solvent was evaporated under reduced pressure and the cold mixture acidified to pH 2 (pH paper) with sodium bisulfate (1N). The aqueous solution was extracted three times with ethyl acetate, the extracts combined and washed with water. After drying the organic phase over magnesium sulfate, filtration and evaporation of the filtrate under reduced pressure, the residue was recrystallized from ethyl acetate/hexanes to give 60.7 g of the title compound. $[\alpha]_D^{25} = +25.4°$ (c=1.1, 1M sodium bicarbonate); m.p. 105°–107° C.

$N^\alpha$-t-Butyloxycarbonyl-p-Nitro-L-Phenylalanyl-Glycine Benzyl Ester (Compound 5)

The carboxylic acid component compound 4 (10.0 g, 32.2 mmol) was dissolved in anhydrous tetrahydrofuran (100 ml) in a 250 ml round-bottom flask equipped with a drying tube. N-Methylmorpoline (3.54 ml, 32.2 mmol) was added and the solution cooled to $-15°$ C. in a dry ice/isopropanol bath. Isobutyl chloroformate (4.18 ml, 32.2 mmol) was added slowly to the stirred solution. The flask was allowed to warm to room temperature to ensure complete formation of the mixed anhydride then re-cooled to $-15°$ C. A solution of glycine benzyl ester p-toluenesulfonate (10.9 g, 32.2 mmol) in dry tetrahydrofuran (100 ml) was cooled to $-15°$ C. and treated with N-methylmorpholine (3.54 ml, 32.2 mmol). This solution was added to the solution of mixed anhydride, the mixture allowed to warm to room temperature and then sitrred for one hour. The solvent was evaporated under reduced pressure and the residue suspended in ethyl acetate for subsequent extractions with 0.1N hydrochloric acid, saturated sodium bicarbonate, and water. After drying the organic phase with magnesium sulfate and filtering, the solution was evaporated to dryness under reduced pressure. The solid residue was recrystallized from chloroform/hexanes to give 12.14 g of the title compound. $[\alpha]_D^{25} = -7.90°$ (c=1.8, chloroform); m.p. 115°–118° C.

$N^\alpha$-t-Butyloxycarbonyl-p-Nitro-L-Phenylalanyl-Glycyl-Methylamide (Compound 6)

A solution of Compound 5 (7.73 g, 16.9 mmol) in methanol (350 ml) was cooled in an ice bath. Methylamine gas was passed through a sodium hydroxide drying tube into the solution. When saturation by the gas was approached (considerable gain in volume) the flask was stoppered and stored overnight in the hood at room temperature. Evaporation of the solvent left a yellow solid which was recrystallized from chloroform/hexanes to give 6.04 g of the title compound. $[\alpha]^{25} = +6.0°$ (c=1.0, methanol); m.p. 182°–184° C.

$N^\alpha$-t-Butyloxycarbonyl-p-(6-Oxoheptanoylamino)-L-Phenylalanyl-Glycyl-Methylamide

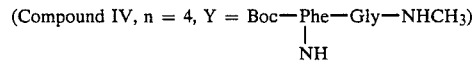
(Compound IV, n = 4, Y = Boc—Phe—Gly—NHCH$_3$)
            |
            NH Compound 6 (5.28 g, 13.9 mmol) was dissolved in methanol (150 ml) and hydrogenated overnight at 1–3 atm. using 10% palladium on charcoal catalyst (0.5 g). The catalyst was removed by filtration through Celite and the filtrate evaporated under reduced pressure, leaving a glassy solid which was used without further purification.

δ-Acetylvaleric acid (2.00 g, 13.9 mmol) was coupled to the amine by the mixed anhydride procedure as described for 6-oxoheptanoic acid p-toluide (Compound IV, n=4, Y=p-methylanilino) giving 5.87 g of a clear glass which was homogeneous by thin layer chromatography (85:10:5 chloroform/methanol/acetic acid) $[\alpha]^{25} = +23.8°$ (c=1.2, methanol).

Preparation of Conjugates

N$^\alpha$-Acetyl-p-{6-(3-[1-Naphthyloxy]-2-Hydroxy-propylamino)-Heptanoylamino}-L-Phenylalanyl-3-Hydroxypropylamide (Compound 15)

The title compounds was synthesized by the method given for Compound 7 using the following quantities: Compound V (R=1-naphthyl) (0.009 g, 0.037 mmol), N$^\alpha$-acetyl-p-(6-oxoheptanoylamino)-L-phenyl-alanyl-3-hydroxypropylamide (0.015 g, 0.037 mmol), sodium cyanoborohydride (0.002 g, 0.037 mmol), in methanol (1 ml). Purification was achieved by high pressure liquid chromatography with the direct injection of 500 μl of the reaction mixture (after destruction of excess cyanoborohydride) onto a semi-preparation C$_{18}$ column using a flow rate of 1.3 ml/min and 52% methanol/0.01N hydrochloric acid as eluant. Evaporation of solvent from the appropriate fractions and lyophilization from water gave 5.0 mg of the hydrochloride salt of the title compound, which was pure by analytical HPLC (1.7 ml/min, 56% methanol/0.01N hydrochloric acid, ret. time=18 min).

N$^\alpha$-t-Butyloxycarbonyl-p-{6-(3-[1-Naphthyloxy]-2-Hydroxypropylamino)-Heptanoylamino}-L-Phenylalanyl-Glycyl-Methylamide (Compound 16)

The title compound was synthesized by the method given for Compound 7 using the following quantities: Compound V (R=1-naphthyl) (0.060 g, 0.236 mmol), N$^\alpha$-t-butyloxycarbonyl-p-(6-oxo-n-heptanoylamino)-L-phenylalanyl-glycyl-methylamide (0.103 g, 0.236 mmol), sodium cyanoborohydride (0.014 g, 0.23 mmol), 5% glacial acetic acid/methanol (5 ml). After stirring the reaction mixture overnight, it was cooled in an ice bath and 0.1N hydrochloric acid added to pH 2 (pH paper). The opaque solution was added to 50 ml 0.1N hydrochloric acid and the resulting solution extracted 3 times with 15 ml ether. Sodium chloride was added to the aqueous phase to saturation and the solution then extracted three times with chloroform. The chloroform fractions were combined and evaporated to dryness to give 60 mg of a glassy foam which was dissolved in chloroform/methanol and subjected to flash chromatography [30 mm×8 in column of silica gel 60 (230-400 mesh); 45:10:5 chloroform/methanol/acetic acid; solvent head drop rate of 2 in/min]. The desired fractions were combined and the solvent removed in vacuo. The residue was re-dissolved in 50 ml water and extracted three times with 20 ml n-butanol. After evaporation of the butanol under reduced pressure, the residue was re-dissolved in a minimum amount of methanol, ether added to precipitate the product and the supernatent decanted. Lyophilization of the precipitate from water gave 13.7 mg of material which was pure by high pressure liquid chromatography (C$_{18}$ column, 2.0 ml/min flow rate, 58% methanol/0.01N hydrochloric acid). The structure was verified by 360 MHz proton NMR.

N$^\alpha$-Acetyl-p-{6-(3-[4-Acetamidophenoxy]-2-Hydroxypropylamino)-Heptanoylamino}-L-Phenylalanyl-3-Hydroxypropylamide (Compound 19)

The title compound was synthesized by the method given for Compound 16 using the following quantities: Compound V (R=p-acetamidophenyl) (0.01 g, 0.037 mmol), N$^\alpha$-acetyl-p-(6-oxo-heptanoylamino)-L-phenylalanyl-3-hydroxypropylamide (0.015 g, 0.037 mmol), sodium cyanoborohydride (0.002 g, 0.037 mmol), methanol (1 ml). Purification was achieved by high pressure liquid chromatography with the direct injection of 500 μl of the reaction mixture (after destruction of remaining cyanoborohydride) onto a semi-preparative C$_{18}$ column using a flow rate of 1.3 m./min and 20% methanol/0.01N hydrochloric acid as eluant. The appropriate fractions were combined and the solvent evaporated under reduced pressure. Lyophilization from water gave 17.2 mg of the hydrochloride salt of the title compound, which was pure by analytical HPLC (flow rate 1.3 ml/min, 44% MeOH/0.01N hydrochloric acid, ret. time=16 min) and thin layer chromatography (50:10:5 chloroform/methanol/acetic acid, R$_f$=0.22).

Pharmacological Activity

The β-adrenergic antagonist derivatives can be tested for biological and pharmacological activity by an in vitro technique. In this test a measurement is taken of the concentration of the derivative required to block a specified dose of isoproterenol (β-adrenergic agonist) in S-49 mouse lymphoma cells as measured by cyclic AMP accumulation therein. Details of the test utilizing S-49 mouse lymphoma cells is set forth in Coffino et al, In Vitro, 14, #1, 140 (1978). The activities of the β-adrenergic derivatives are expressed as the relative potencies of the unmodified drug, i.e., the β-adrenergic antagonist to that of the derivative drug.

Biological Testing Results

A number of β-adrenergic antagonist derivatives both congeners and conjugates were tested in vitro according to the method set forth above.

Table 1 below presents the relative biological activities of the indicated compounds.

TABLE 1

In Vitro Biological Activity of Propranolol and Practolol Derivatives $$R-OCH_2-\underset{\underset{OH}{|}}{CH}-CH_2-NH-\underset{\underset{CH_3}{|}}{CH}-(CH_2)_n-CO-NH-X$$

| Compound # | R | n | X$^a$ | Rel. Potency$^b$ |
|---|---|---|---|---|
| 7 | 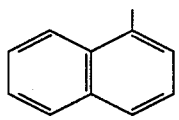 | 2 |  | 6.8 × 10$^{-5}$ |
| 8 | " | 3 | " | 6.8 × 10$^{-5}$ |
| 9 | " | 4 | " | 4.5 × 10$^2$ |
| 10 | " | 5 | " | 3.7 × 10$^{-2}$ |

TABLE 1-continued
In Vitro Biological Activity of Propranolol and Practolol Derivatives $$R-OCH_2-\underset{\underset{OH}{|}}{CH}-CH_2-NH-\underset{\underset{CH_3}{|}}{CH}-(CH_2)_n-CO-NH-X$$

| Compound # | R | n | X[a] | Rel. Potency[b] |
|---|---|---|---|---|
| 11 | " | 4 | 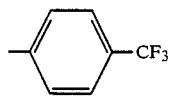 —CF₃ | 8.75 |
| 12 | " | 4 | 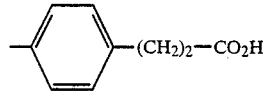 —(CH₂)₂—CO₂H | $8.8 \times 10^{-1}$ |
| 13 | " | 4 | 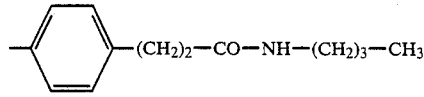 —(CH₂)₂—CO—NH—(CH₂)₃—CH₃ | $4.5 \times 10^{-2}$ |
| 14 | " | 4 | —(CH₂)₃—CH₃ | $9.1 \times 10^{-1}$ |
| 15 | " | 4 | Ac—Phe—HPA | $1.75 \times 10^{-1}$ |
| 16 | " | 4 | Boc—Phe—Gly—NH—CH₃ | $7.8 \times 10^{-4}$ |
| 17 | CH₃CONH—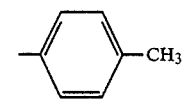— | 4 | 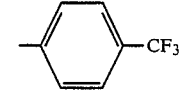 —CH₃ | $2.1 \times 10^{1}$ |
| 18 | " | 4 | 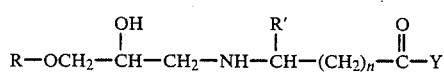 —CF₃ | 6.0 |
| 19 | " | 4 | Ac—Phe—HPA | 1.5 |

[a]Ac = CH₃—CO; Boc = (CH₃)₃C—O—CO; HPA = NH—(CH₂)₃—OH; Phe = p-amino-phenylalanyl; Gly = glycyl
[b]Potency relative to the parent compound (propranolol or practolol) as estimated by blocking isoproterenol-promoted cyclic AMP release in S49 cells.

We claim:

1. β-adrenergic antagonist compounds having the formula:

$$R-OCH_2-\underset{\underset{OH}{|}}{CH}-CH_2-NH-\underset{\underset{R'}{|}}{CH}-(CH_2)_n-\overset{\overset{O}{\|}}{C}-Y$$

wherein R = an aryl or substituted aryl or heterocyclic or substituted heterocyclic moiety selected from the group consisting of:

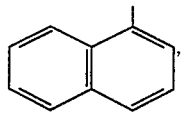,

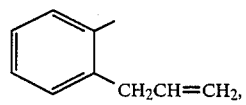

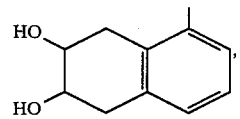,

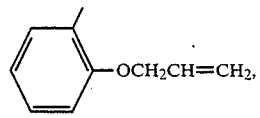,

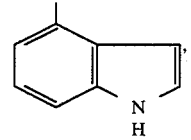,

-continued

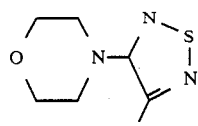

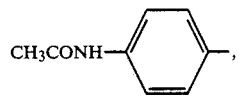

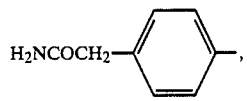

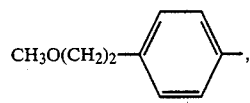

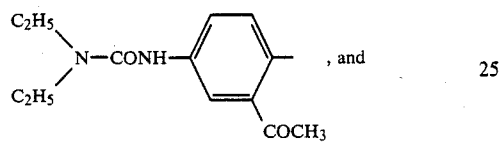, and

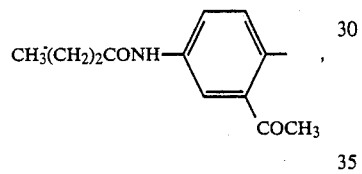

R'=H, —CH₃, or short chain alkyl moiety; n is an integer between 1 and 15; and Y=—O—A—X, or —NH—A—X, where A—a linking functional grouping selected from alkyl, aryl or aralkyl, and X=carrier moiety selected from polypeptides, peptide hormones, proteins, or antibodies each having a molecular weight of between about 75 and 10,000 daltons wherein said carrier moiety in and of itself has essentially no biological activity.

2. The compound of claim 1 wherein X is selected from polypeptides wherein said polypeptides have essentially no biological activity.

3. The compound of claim 2 wherein the polypeptides are selected from homooligopeptide blocks.

4. The compounds of claim 1 wherein the carrier moiety is a defined peptide.

5. The compounds of claim 1 wherein the carrier moiety is a protein.

6. The compounds of claim 1 wherein the carrier moiety is a naturally occurring peptide.

7. The compound N$^\alpha$-acetyl-p-{6-(3-[4-acetamidophenoxy]-2-hydroxypropylamino)-heptanoylamino}-L-phenylalanyl-3-hydroxypropylamide and pharmaceutically acceptable salts thereof.

8. A β-andrenergic antagonist compound of the formula:

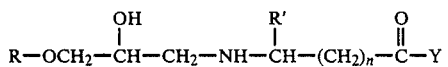

wherein R is selected from the group consisting of:

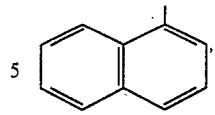

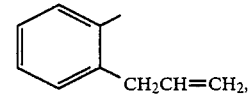

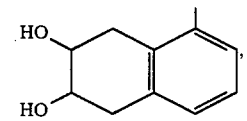

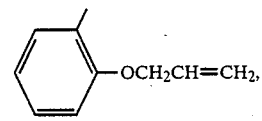

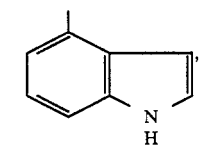

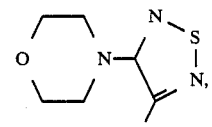

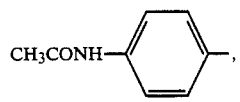

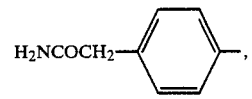

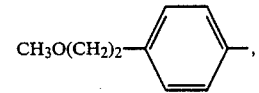

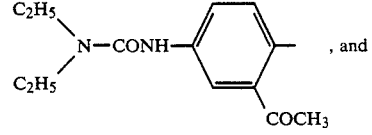, and

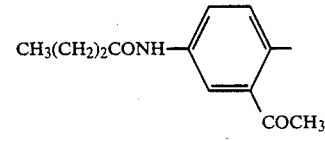

R'=—H, —CH₃, or short chain alkyl moiety; n is an integer between 1 and 15; and Y=—O—A—X, or —NH—A—X, where A=a linking functional grouping selected from alkyl, aryl or aralkyl and X=a carrier moiety having a molecular weight in the range of 75 to 10,000 daltons wherein said carrier itself has essentially no biological activity and wherein X is a peptide carrier of the formula:

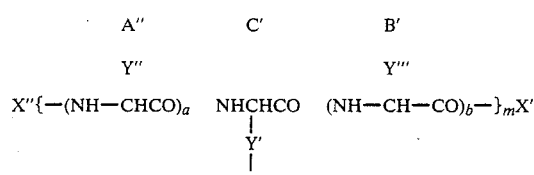

wherein
- A' and B' are oligopeptide blocks wherein the amino acid residues are the same or different with predesigned sequences;
- C' is an amino acid residue to which the congener is bound;
- X" is an amine blocking group or H;
- X' is a carboxyl blocking group, or H;
- Y" is a general amino acid residue side chain;
- Y''' is a general amino acide residue side chain;
- Y' is a side chain on the amino acid residue to which the congener is bound where a=b, a=b, a or b are each be 0 or any samll integer; and m is 1, 2 or 3.

9. The β-andrenergic antagonist compound of claim 8 wherein X is a carrier consisting essentially of identical amino acids.

10. The β-andrenergic antagonist compound of claim 8 wherein the a=b, and a or b are 0 or an integer from 1 to 9.

11. The β-andrenergic antagonist compound of claim 10 wherein A' and B' are selected from oligopeptide blocks wherein a and b are each selected from an integer from 1–3.

12. The β-andrenergic antagonist compound of claim 8 wherein X=a carrier moiety having a molecular weight in the range of 200 and 10,000 daltons, wherein said carrier moiety X is selected from synthetic peptides selected from polyserine, polyglycine, polytyrosine, polythreonine, polycysteine, polyaspartic acid or polyglutamic acid.

* * * * *